(12) United States Patent
Sukthankar et al.

(10) Patent No.: US 9,848,947 B2
(45) Date of Patent: Dec. 26, 2017

(54) DEVICES AND METHODS FOR PROSTATE TISSUE ABLATION AND/OR RESECTION

(71) Applicant: Boston Scientific Scimed, Inc., Maple Grove, MN (US)

(72) Inventors: Sujat Sukthankar, Shrewsbury, MA (US); Jianmin Li, Lexington, MA (US); Kenneth P. Reever, Hopedale, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 457 days.

(21) Appl. No.: 14/547,591

(22) Filed: Nov. 19, 2014

(65) Prior Publication Data

US 2015/0157397 A1 Jun. 11, 2015

Related U.S. Application Data

(60) Provisional application No. 61/914,790, filed on Dec. 11, 2013.

(51) Int. Cl.
*A61B 18/14* (2006.01)
*A61B 18/00* (2006.01)

(52) U.S. Cl.
CPC . *A61B 18/1485* (2013.01); *A61B 2018/00011* (2013.01); *A61B 2018/00202* (2013.01); *A61B 2018/00208* (2013.01); *A61B 2018/00547* (2013.01); *A61B 2018/00577* (2013.01); *A61B 2018/1407* (2013.01); *A61B 2018/1467* (2013.01)

(58) Field of Classification Search
CPC ............... A61B 2018/1467; A61B 2018/1407
See application file for complete search history.

(56) References Cited

U.S. PATENT DOCUMENTS

| | | | | |
|---|---|---|---|---|
| 5,683,384 A | * | 11/1997 | Gough | A61B 18/1477 606/33 |
| 5,735,847 A | * | 4/1998 | Gough | A61B 18/1477 606/15 |
| 5,810,802 A | * | 9/1998 | Panescu | A61B 5/0422 374/E1.005 |
| 5,810,806 A | * | 9/1998 | Ritchart | A61B 10/0266 604/21 |

(Continued)

FOREIGN PATENT DOCUMENTS

| | | | | |
|---|---|---|---|---|
| EP | 2851027 A1 | * | 3/2015 | ......... A61B 18/1492 |
| GB | 2311468 A | * | 10/1997 | ............. A61B 18/14 |

(Continued)

*Primary Examiner* — Ruth Ilan
(74) *Attorney, Agent, or Firm* — Bookoff McAndrews, PLLC (57) ABSTRACT

According to one aspect of the present disclosure, a medical device may include a shaft assembly. The shaft assembly may include a sheath having a first lumen. The shaft assembly may also include a rotatable shaft extending through the first lumen. The rotatable shaft may be rotatable relative to the sheath, and may have a second lumen and a side opening. The shaft assembly may also include an electrode extending through the second lumen and the side opening, and radially outwardly from the rotatable shaft. The electrode may be movable relative to the rotatable shaft.

15 Claims, 7 Drawing Sheets

(56) References Cited

U.S. PATENT DOCUMENTS

| | | | | |
|---|---|---|---|---|
| 6,071,274 A | * | 6/2000 | Thompson | A61B 18/1492 604/528 |
| 6,071,279 A | * | 6/2000 | Whayne | A61B 18/1492 606/41 |
| 6,287,304 B1 | * | 9/2001 | Eggers | A61B 18/1492 606/37 |
| 6,540,693 B2 | * | 4/2003 | Burbank | A61B 10/0266 600/564 |
| 7,534,242 B2 | * | 5/2009 | Buehlmann | A61B 18/1492 600/564 |
| 9,060,782 B2 | * | 6/2015 | Daniel | A61B 18/1477 |
| 9,301,795 B2 | * | 4/2016 | Fischell | A61M 25/0084 |
| 9,392,971 B2 | * | 7/2016 | Asirvatham | A61N 1/20 |
| 2005/0171536 A1 | * | 8/2005 | Phan | A61B 18/1492 606/49 |
| 2008/0300454 A1 | * | 12/2008 | Goto | A61B 17/221 600/104 |
| 2013/0324987 A1 | * | 12/2013 | Leung | A61B 18/0218 606/20 |
| 2015/0351835 A1 | * | 12/2015 | Hwang | A61B 18/1492 606/41 |
| 2016/0242661 A1 | * | 8/2016 | Fischell | A61B 5/4035 |
| 2016/0331452 A1 | * | 11/2016 | Oguni | A61B 1/00 |
| 2017/0128129 A1 | * | 5/2017 | Kelly | A61B 18/1492 |

FOREIGN PATENT DOCUMENTS

| | | | | |
|---|---|---|---|---|
| IT | WO 2015140741 A1 | * | 9/2015 | A61B 18/1492 |
| JP | 2004073582 A | * | 3/2004 | A61B 17/32056 |
| WO | WO 2009036457 A1 | * | 3/2009 | A61B 18/14 |

\* cited by examiner

DEVICES AND METHODS FOR PROSTATE TISSUE ABLATION AND/OR RESECTION

CROSS-REFERENCE TO RELATED APPLICATIONS

This application claims the benefit of priority from U.S. Provisional Application No. 61/914,790, filed on Dec. 11, 2013, which is incorporated by reference herein in its entirety.

FIELD OF THE DISCLOSURE

Embodiments of the present disclosure generally relate to medical devices and related methods of use. In particular, embodiments of the present disclosure relate to devices for ablation and/or resection of tissue.

BACKGROUND OF THE DISCLOSURE

Benign prostatic hyperplasia ("BPH") is a condition characterized by an undesirable increase in the number of cells in prostate tissue. Such enlargement may adversely affect the urinary tract by constricting the urethra, possibly leading to painful urination, decreased urine flow, difficulty starting or stopping urine flow, nocturnal urination, incomplete voiding, and other symptoms.

Surgery is one of the more effective ways of treating BPH. A common minimally invasive surgical procedure for treating BPH is transurethral resection of the prostate ("TURP"). Existing cystoscopic devices, however, may be difficult to stabilize and control when performing TURP or other surgical procedures. As a result, there is a risk of resecting or otherwise damaging healthy tissue, which may lead to further complications.

It may be, therefore, useful to provide a medical device with enhanced stability and control to enhance a user's ability to accurate remove unwanted tissue.

SUMMARY OF THE DISCLOSURE

According to one aspect of the present disclosure, a medical device may include a shaft assembly. The shaft assembly may include a sheath having a first lumen. The shaft assembly may also include a rotatable shaft extending through the first lumen. The rotatable shaft may be rotatable relative to the sheath, and may have a second lumen and a side opening. The shaft assembly may also include an electrode extending through the second lumen and the side opening, and radially outwardly from the rotatable shaft. The electrode may be movable relative to the rotatable shaft.

According to another aspect of the present disclosure, a medical device may include a shaft assembly. The shaft assembly may include a sheath having a first lumen. The shaft assembly may also include a rotatable shaft extending through the first lumen. The rotatable shaft may be rotatable relative to the sheath and may have a second lumen and side openings. The shaft assembly may also include a plurality of electrodes including proximal sections extending through the second lumen and the side openings, and distal sections extending radially outwardly from the rotatable shaft. Each of the electrodes may be independently movable relative to the rotatable shaft.

According to yet another aspect of the present disclosure, a method for removing tissue in an organ may include inserting a medical device into a passage through the organ. The passage may be formed at least in part by the tissue. The method may also include positioning a shaft assembly of the medical device in the passage. The shaft assembly may include a sheath, a shaft extending through the sheath, and an electrode extending radially outwardly from the shaft. The method may also include moving the electrode relative to the sheath. The method may also include energizing the electrode with electrical energy, moving the energized electrode relative to the sheath, and engaging the tissue with the energized electrode.

Additional characteristics, features, and advantages of the described embodiments will be set forth in part in the description that follows, and in part will be apparent from the description, or, may be learned by practicing the disclosure. The disclosed subject matter can be realized and attained by way of the elements and combinations particularly pointed out in the appended claims.

It is to be understood that both the foregoing general description and the following detailed description are exemplary and explanatory only, and are not restrictive of the described embodiments, as claimed.

BRIEF DESCRIPTION OF THE DRAWINGS

The accompanying drawings, which are incorporated here and constitute a part of this specification, illustrate exemplary embodiments of the present disclosure and, together with the description, serve to explain the principles of the disclosure.

DESCRIPTION OF THE EMBODIMENTS

Reference will be made in detail to embodiments of the present disclosure, examples of which are illustrated in the accompanying drawings. Wherever possible, the same reference numbers will be used throughout the drawings to refer to the same or like parts.

Figure 1:
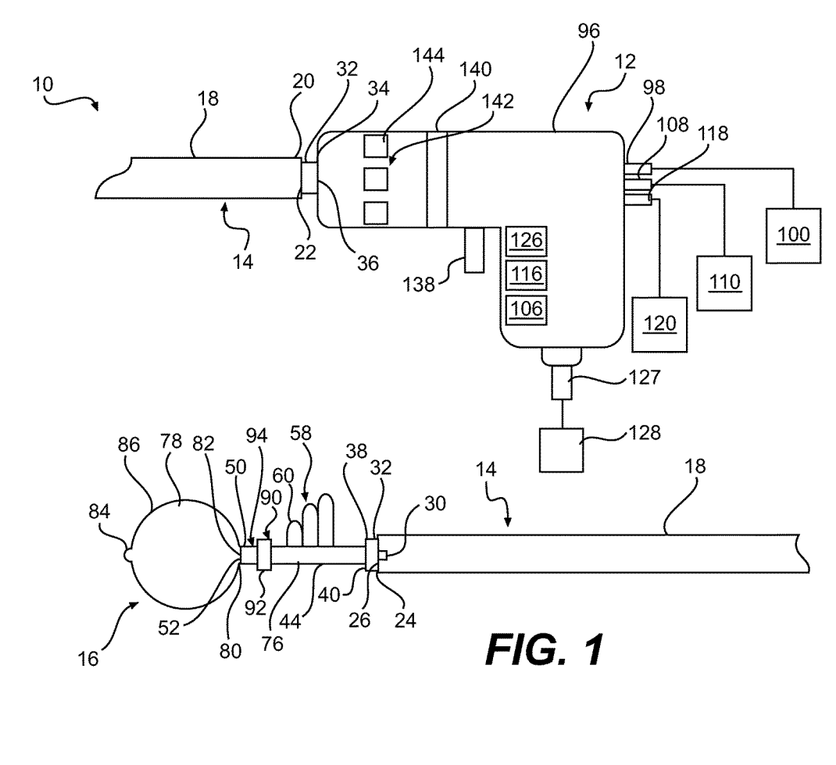
FIG. 1 shows a side view of an exemplary medical device, according to aspects of the present disclosure.

FIG. 1 shows a side view of an exemplary embodiment of a medical device 10, according to an embodiment of the present disclosure. The medical device 10 may include a handle assembly 12, a shaft assembly 14, and an anchor unit 16. The handle assembly 12 may be located at a proximal section of the medical device 10. The handle assembly 12 may include a handle housing 96, which may be designed for ease of use and ergonomics. The handle housing 96 may include one or more ports, such as an aspiration port 98, an irrigation fluid port 108, and an inflation fluid port 118, which may be in communication with one or more working channels. The aspiration port 98, the irrigation fluid port 108, and the inflation fluid port 118 may be in fluid communication with a vacuum source 100, an irrigation fluid source 110, and an inflation fluid source 120, respectively. These sources 100, 110, 120 may be located external to the handle assembly 12. Alternatively, the sources 100, 110, 120 may be located on or within the handle housing 96. It is also contemplated that the handle assembly 12 may have additional ports and/or lumens for other diagnostic and/or treatment devices, such as for a guidewire and/or surgical instruments.

The handle housing 96 may also include an aspiration actuator 106, an irrigation fluid actuator 116, and an inflation fluid actuator 126. The aspiration actuator 106 may be configured to control the outflow of fluid, tissue, debris, and/or other material through the aspiration port 98. The irrigation fluid actuator 116 may be configured to regulate the flow of irrigation fluid through the handle housing 96. The inflation fluid actuator 126 may be configured to control the flow of inflation fluid through the handle housing 96. The handle housing 96 may further include a rotation member 140 and an electrode adjustment unit 142. The rotation member 140 may include one or more electrical conductors and one or more fluid passages.

The electrode adjustment unit 142 may be coupled to the rotation member 140 and may include at least one electrode adjustment actuator 144. The electrode adjustment actuator 144 may be configured to adjust lengths of one or more electrodes 58. The one or more electrodes 58 may include ablation electrodes used for ablating tissue, and/or resection electrodes for resecting tissue. It is contemplated that ablation electrodes may also be used for resection, and vice versa. The electrode adjustment actuator 144 may include, for example, a spool (not shown) configured to rotate in a first direction to wind portions of the one or more electrodes 58 onto the outer surface of the spool, thus pulling the one or more electrodes 58 in a proximal direction; and to rotate in a second direction to unwind portions of the one or more electrodes 58 from the outer surface of the spool, thus pushing the one or more electrodes 58 in a distal direction. Alternatively, the electrode adjustment actuator 144 may include a pin (not shown) coupled to the one or more electrodes 58, configured to extend through a slot (not shown) in the side of the handle housing 96, for manipulation by the user. The user may slide the pin in a proximal direction to pull the one or more electrodes 58 in the proximal direction, and may slide the pin in a distal direction to push the one or more electrodes 58 in the distal direction. It is also contemplated that each electrode 58 may be operatively coupled to its own electrode adjustment actuator 144, so that each electrode 58 may be adjusted independently of the other electrodes 58.

The handle housing 96 additionally may include a radiofrequency ("RF") actuator 138 connected to an RF energy connector 127, which may be externally coupled to an RF source 128. In alternative embodiments, the RF connector 127 and the RF source 128 may be mounted on or within the handle housing 96. The RF actuator 128 may regulate the RF energy applied to the electrodes 58 from the RF connector 127 and the RF source 128.

The handle assembly 12 may be coupled at its distal end to the shaft assembly 14. Handle assembly 12 may have any useful shape or orientation, for example, the gun shape illustrated in FIG. 1, but it may also be shaped as a cylinder along one longitudinal axis or as a cylinder with a bend that is obtuse to the longitudinal axis; although these examples are not meant to be limiting. Handle assembly 12 may further include grippable features such as an elastomeric coating or finger grooves to allow a location to position the user's fingers on the handle assembly 12. The shaft assembly 14 may be insertable into a first sheath 18, and the shaft assembly 14 may include a second sheath 32, a shaft 44, and one or more electrodes 58. The first sheath 18 may include a proximal end 20 having a proximal opening 22, a distal end 24 having a distal opening 26, and a central lumen 28 (FIG. 4) extending between the proximal end 20 and the distal end 24. An imaging device 30 may be positioned adjacent to the distal end 24. The imaging device 30 may include, for example, a lens, single-chip sensor, multiple chip sensor, and/or or fiber optic device. The imaging device 30 may also include a light source (not shown), such as an incandescent or light-emitting diode (LED) light source, whose intensity may be adjusted to achieve optimum imaging. The imaging device 30 may be in electrical communication with a processor and/or monitor and may provide images or video of areas of a subject's body within its field of view.

The first sheath 18 may slidably receive the second sheath 32 in its central lumen 28. The second sheath 32 may include a proximal end 34 having a proximal opening 36, a distal end 38 having a distal opening 40, and a central lumen 42 (FIG. 4) that extends between the proximal end 34 and the distal end 38. The proximal end 34 of the second sheath 32 may be coupled to the handle assembly 12. The second sheath 32 may be extended distally out of the distal opening 26 at the distal end 24 of the first sheath 18, and may be retracted proximally into the distal end 24 of the first sheath 18.

The rotatable shaft 44 may be slidably received by the central lumen 42 of the second sheath 32. The rotatable shaft 44 may include a proximal end 46 (FIG. 5) coupled to the handle assembly 12. The proximal end 46 of the rotatable shaft 44 may include a proximal opening 48 (FIG. 5), the distal end 50 of the shaft 44 may include a distal opening 52, and the rotatable shaft 44 may include a central lumen 54 extending between the proximal end 46 and the distal end 50.

One or more of the first sheath 18, second sheath 32, and shaft 44 may be flexible, to allow navigation through curved lumens in a subject's body. Additionally or alternatively, one or more of the first sheath 18, second sheath 32, and shaft 44 may be rigid, giving a user precise control over movements. It is also contemplated that one or more of the first sheath 18, second sheath 32, and shaft 44 may be partially flexible and partially rigid. The first sheath 18, second sheath 32, and shaft 44 may have any suitable cross-sectional shape and size that would allow passage through a body lumen, such as the urethra.

The anchor unit 16 may include an anchor member, such as an inflatable balloon 78, for anchoring the medical device 10 within a subject's body during performance of a medical procedure. Anchor unit 16 may also comprise a wire basket or a collapsible bulb made, for example, of a foam material; these examples are not meant to be limiting. The balloon 78 may be coupled to the distal end 50 of the shaft 44. The balloon 78 may include a distal end 84 and a proximal end 80. The balloon 78 may have a proximal opening 82. The balloon 78 may have inflated and uninflated states. The balloon 78 may be made from an electrically non-conductive polymer, such as Pebax, nylon, polyester, or block-copolymer. The outer surface 86 of the balloon 78 may be made from or coated with a non-hydrophilic material, such as non-hydrophilic polyurethane. Balloon 78 may be compliant, non-compliant, or have an otherwise controlled compliance at the inflation pressure used to inflate the balloon 78.

A spacer 90 may be mounted at the distal end 50, such that the spacer 90 extends radially outwardly from the outer surface of the shaft 44. The spacer 90 may include a cylindrical sleeve 92. A distal end of the spacer 90 may be configured to engage tissue to help position the medical device 10 for performance of a procedure. The spacer 90 may be radiopaque, sonolumescent, or otherwise imageable to allow a user to image its positioning in the patient's body if desired.

Figure 2A:
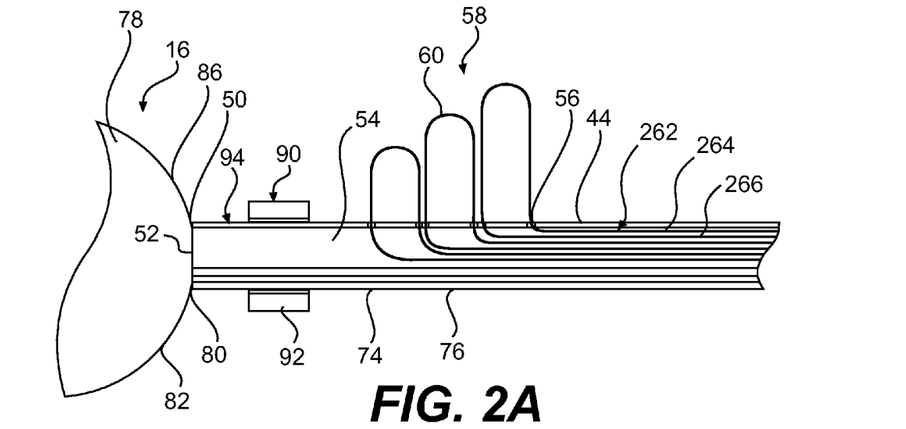
FIGS. 2A and 2B are cross-sectional views of exemplary distal sections of a rotatable shaft, according to aspects of the present disclosure.
Figure 2B:
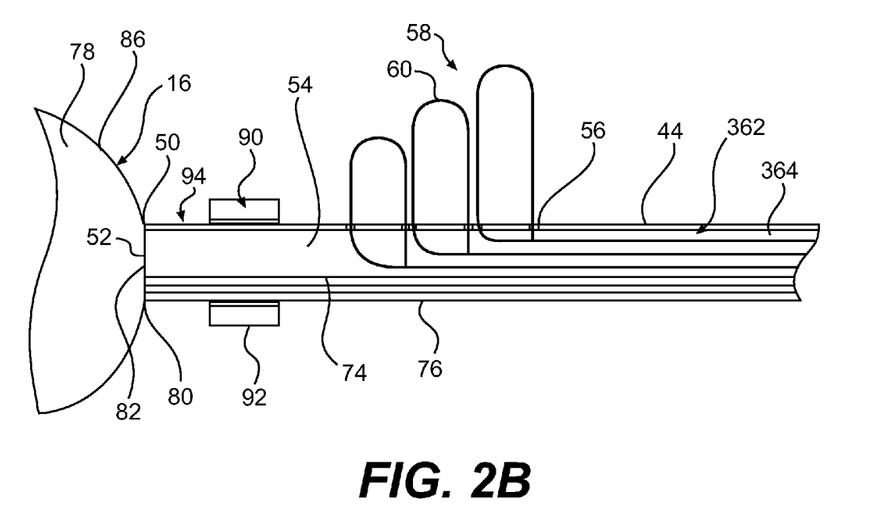

As shown in FIGS. 2A and 2B, the shaft 44 may include one or more side openings 56 positioned between the spacer 90 and the distal end of the second sheath 32. The side openings 56 may be configured to slidably receive the electrodes 58. The electrodes 58 may be formed of any suitable currently known, related art, and/or later developed biocompatible flexible and conductive material, such as, but not limited to, polymers, metals, and/or alloys. Portions of the electrodes 58 may be insulated. For example, portions of the electrodes outside of the side openings 56 may be uninsulated, while portions of the electrodes inside the side openings 56 and the rotatable shaft 44 may be insulated by being covered with a non-conductive jacket or coating.

The medical device 10 may include multiple electrodes 58 in the form of loops 60. End sections of the loops 60 may extend through the side openings 56, and may extend radially outwardly from the outer surface of the shaft 44. Proximal sections of the loops 60 may extend through the central lumen 54 of the shaft 44 to the handle assembly 12. FIG. 2A shows proximal sections 262 including pairs of proximal legs 264 and 266. FIG. 2B shows proximal sections 362 including single legs 364. Using the handle assembly 12, a user may pull the proximal sections of the loops 60 proximally to retract the end sections of the loops 60 through the side openings 56 and into the central lumen 54, and may push the proximal sections distally to extend the end sections out of the side openings 56 and radially outwardly from the shaft 44.

For example, in one embodiment, the proximal sections of the loops 60 may control the extension of each loop 60 by sliding the loops 60 along the length of the device 10 such that the loops 60 cannot slide distally, and bend radially from the axis of the medical device 10, extending the loops 60 radially. In the handle assembly 12, this may be actuated with sliding buttons connected to each loop 60 which allow the user to push the loops 60 distally. In another embodiment, the proximal sections of each loop 60 may extend radially from the handle assembly 12 and be insulated proximally. Pressing these proximal portions of the loops 60 inward towards the axis of the medical device 10 will result in an axial and distal force upon each loop 60 which will cause the loop(s) 60 to extend radially from the medical device 10 at their distal ends.

In one embodiment, the leg 264 may act as an active electrode, while the leg 266 may act as a return electrode, or vice versa, and thus, the electrodes 58 may be bipolar. Alternatively, the legs 264 and 266 may act as one of the active and return electrodes, and thus, the electrodes 58 may be monopolar. The outer surface 76 of the shaft 44 may act as the other of the active and return electrodes. Alternatively, the leg 364 may act as one of the active and return electrodes, and the outer surface 76 may act as the other of the active and return electrodes. If a monopolar system is used, the return electrode may be situated outside the body in contact with the skin of a patient and separate from the medical device 10.

It is also contemplated that in some embodiments, the electrodes 58 may not be aligned along the length of the shaft 44. For example, one or more of the electrodes 58 may be circumferentially offset or displaced from one or more of the other electrodes 58. One or more of the side openings 56 may also be circumferentially offset or displaced from one or more of the other side openings 56. In such an arrangement, the legs 262 and 362 may not be stacked radially, but rather, may lie substantially side-by-side circumferentially, allowing the diameter of the shaft 44 to be reduced while still accommodating the legs 262 and 362. This reduction may provide for a more compact design of the electrodes 58 in the shaft 44 and in the handle assembly 12. The side-by-side circumferential arrangement may also help ensure that each of the electrodes 58 may be moved relative to the other electrodes 58, without being impeded by the other electrodes 58.

Figure 3A:
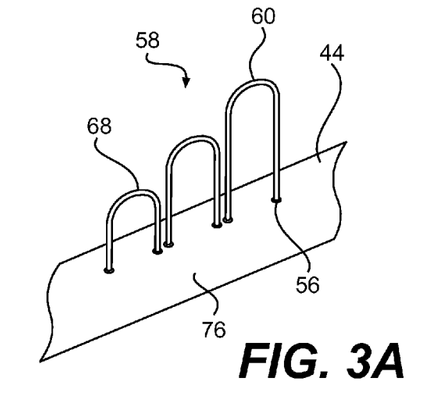
FIGS. 3A to 3D are perspective views of exemplary embodiments of shaft assemblies, according to aspects of the present disclosure.

FIGS. 3A to 3D illustrate exemplary embodiments of the shaft assembly. FIG. 3A shows the rotatable shaft 44 with one or more side openings 56, through which the electrodes 58, in the form of wire loops 68, extend. The side openings 56 may have a round shape to receive the wire loops 68. Proximal sections of the wire loops 68 may be similar to the proximal section 262 (FIG. 2A) or the proximal section 362 (FIG. 2B). The wire loops 68 may be selectively extended out from or retracted into the side openings 56, by pushing or pulling on the proximal sections. It is contemplated that one or more of the side openings 56 and one or more of the wire loops 68 may be aligned along the length of the shaft 44. Alternatively, one or more of the side openings 56 and one or more of the wire loops 68 may be circumferentially displaced or offset from one or more of the others.

Figure 3B:
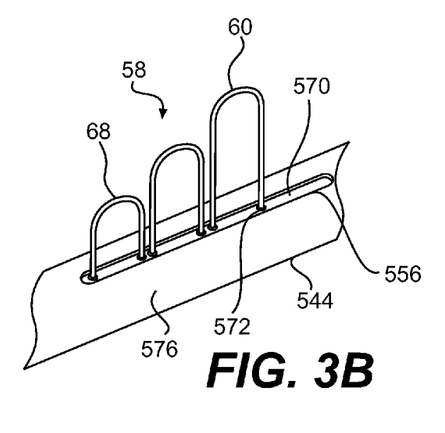

Alternatively, as shown in FIG. 3B, a rotatable inner shaft 570 may have side openings 572, through which the wire loops 68 may extend. Proximal sections of the wire loops 68 may be similar to the proximal section 262 (FIG. 2A) or the proximal section 362 (FIG. 2B), and may extend through a lumen of the inner shaft 570. The wire loops 68 may be selectively extended out from or retracted into the side openings 572, by pushing or pulling on the proximal sections. The rotatable inner shaft 570 may be slidably received within a lumen of an outer shaft 544. The outer shaft 544 may include a slot 556. The slot 556 may extend longitudinally along the outer shaft 544. The wire loops 68 may extend through the slot 556. The outer surface 576 of the outer shaft 544 may act as one of the active and return electrodes, when the electrodes 58 are monopolar. It is contemplated that one or more of the side openings 572 and one or more of the wire loops 68 may be aligned along the length of the inner shaft 570. Alternatively, one or more of the side openings 572 and one or more of the wire loops 68 may be circumferentially displaced or offset from one or more of the others. In such an embodiment, the outer shaft 544 may include a plurality of slots 556 to accommodate the offset opening(s) 572 and/or wire loop(s) 68.

The inner shaft 570 and the outer shaft 544 may be rotatable as a unit. The rotatable inner shaft 570 and the outer shaft 544 may be longitudinally slidable relative to each other. This longitudinal sliding may allow longitudinal adjustment of the position of the wire loops 68. Retraction/extension of the wire loops 68, and/or longitudinal sliding of the wire loops 68, provides the user with enhanced control of the wire loops 68 when performing a procedure.

Figure 3C:
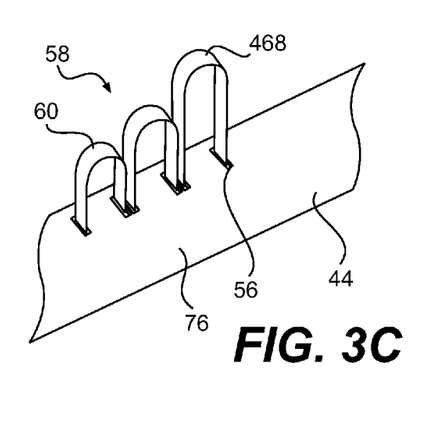

Alternatively, as shown FIG. 3C, the rotatable shaft 44 may include side openings 56 having relatively rectangular shapes to allow passage of electrodes 58 in the form of ribbons or blades 468. Proximal sections of the ribbons 468 may be similar to the proximal section 262 (FIG. 2A) or the proximal section 362 (FIG. 2B). The ribbons 468 may be selectively extended out from or retracted into the side openings 56, by pushing or pulling on the proximal sections. It is contemplated that one or more of the side openings 56 and one or more of the ribbons 468 may be aligned along the length of the shaft 44. Alternatively, one or more of the side openings 56 and one or more of the ribbons 468 may be circumferentially displaced or offset from one or more of the others.

Figure 3D:
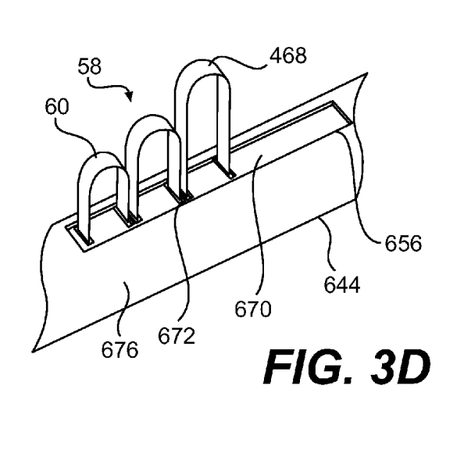

Alternatively, as shown in FIG. 3D, a rotatable inner shaft 670 may have side openings 672, through which the ribbons 468 may extend. Proximal sections of the ribbons 468 may be similar to the proximal section 262 (FIG. 2A) or the proximal section 362 (FIG. 2B), and may extend through a lumen of the inner shaft 670. The ribbons 468 may be selectively extended out from or retracted into the side openings 672, by pushing or pulling on the proximal sections. The rotatable inner shaft 670 may be slidably received within a lumen of an outer shaft 644. The outer shaft 644 may include a slot 656. The slot 656 may extend longitudinally along the outer shaft 644. The ribbons 468 may extend through the slot 656. The outer surface 676 of the outer shaft 644 may act as one of the active and return electrodes when the electrodes 58 are monopolar.

The inner shaft 670 and the outer shaft 644 may be rotatable as a unit. The rotatable inner shaft 670 and the outer shaft 644 may be longitudinally slidable relative to each other. This longitudinal sliding may allow longitudinal adjustment of the position of the ribbons 468. Retraction/extension of the ribbons 468, and/or longitudinal sliding of the ribbons 468, provides the user with enhanced control of the ribbons 468 when performing a procedure.

It is contemplated that one or more of the side openings 672 and one or more of the ribbons 468 may be aligned along the length of the inner shaft 670. Alternatively, one or more of the side openings 672 and one or more of the ribbons 468 may be circumferentially displaced or offset from one or more of the others. In such an embodiment, the outer shaft 644 may include a plurality of slots 656 to accommodate the offset opening(s) 672 and/or ribbon(s) 468.

In some embodiments, the proximal sections of the electrodes may control the extension of each electrode by sliding the electrodes along the length of the device 10 such that the electrodes cannot slide distally, and bend radially from the axis of the medical device 10, extending the electrodes radially. In the handle assembly 12, this may be actuated with sliding buttons connected to each of the electrodes which allow the user to push the electrodes distally. In other embodiments, the proximal sections of each of the electrodes may extend radially from the handle assembly 12 and be insulated proximally. Pressing these proximal portions of the electrodes inward towards the axis of the medical device 10 will result in an axial and distal force upon each of the electrodes which will cause the electrode(s) to extend radially from the medical device 10 at their distal ends.

Figure 4:
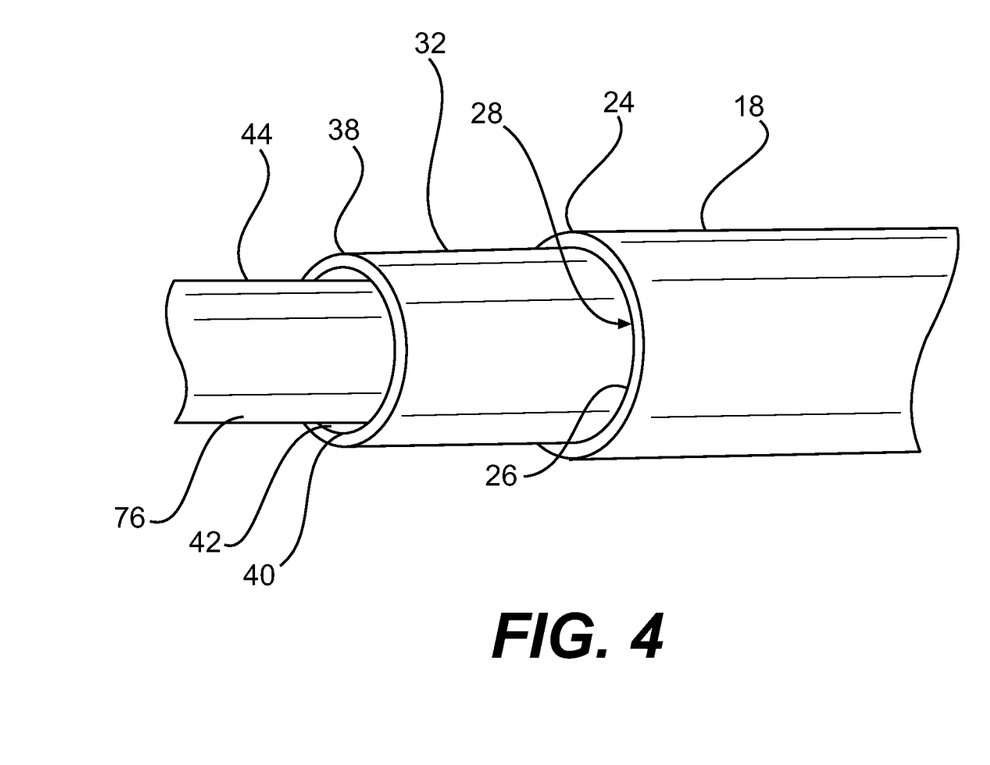
FIG. 4 is a perspective view of an exemplary embodiment of a shaft assembly, according to aspects of the present disclosure.

FIG. 4 illustrates an exemplary arrangement of a portion of the shaft assembly 14. The shaft 44 may extend distally beyond the distal end 38 of the second sheath 32. The second sheath 32 may extend distally beyond the distal end 24 of the first sheath 18. The lumen 42 of the second sheath 32 may act as an aspiration lumen. When negative pressure is applied to the lumen 42, a vacuum force may be created within the lumen 42 and at the distal opening 40. The negative pressure may be used to remove material, such as tissue debris, bodily fluids, and/or irrigation fluids, out from the treatment region during a procedure. It is contemplated that the distal opening 40 may be positioned adjacent to the electrodes 58 to assist with the removal of material.

The central lumen 54 of the shaft 44 may receive irrigation fluid, and direct the irrigation fluid out of the side openings 56. The central lumens of the shafts 570 and 670 (FIGS. 3B and 3D) may receive irrigation fluid, and direct the irrigation fluid out of the side openings 572 and 672, respectively. Thus, irrigation fluid may be provided at the treatment area, at the location where the electrodes 58 are removing (e.g., ablating and/or resecting) tissue. This is where irrigation is most needed during performance of a procedure. The irrigation fluid may flush the treatment area to cool down the tissue, remove tissue fragments, and/or rinse the imaging device 30.

Figure 5:
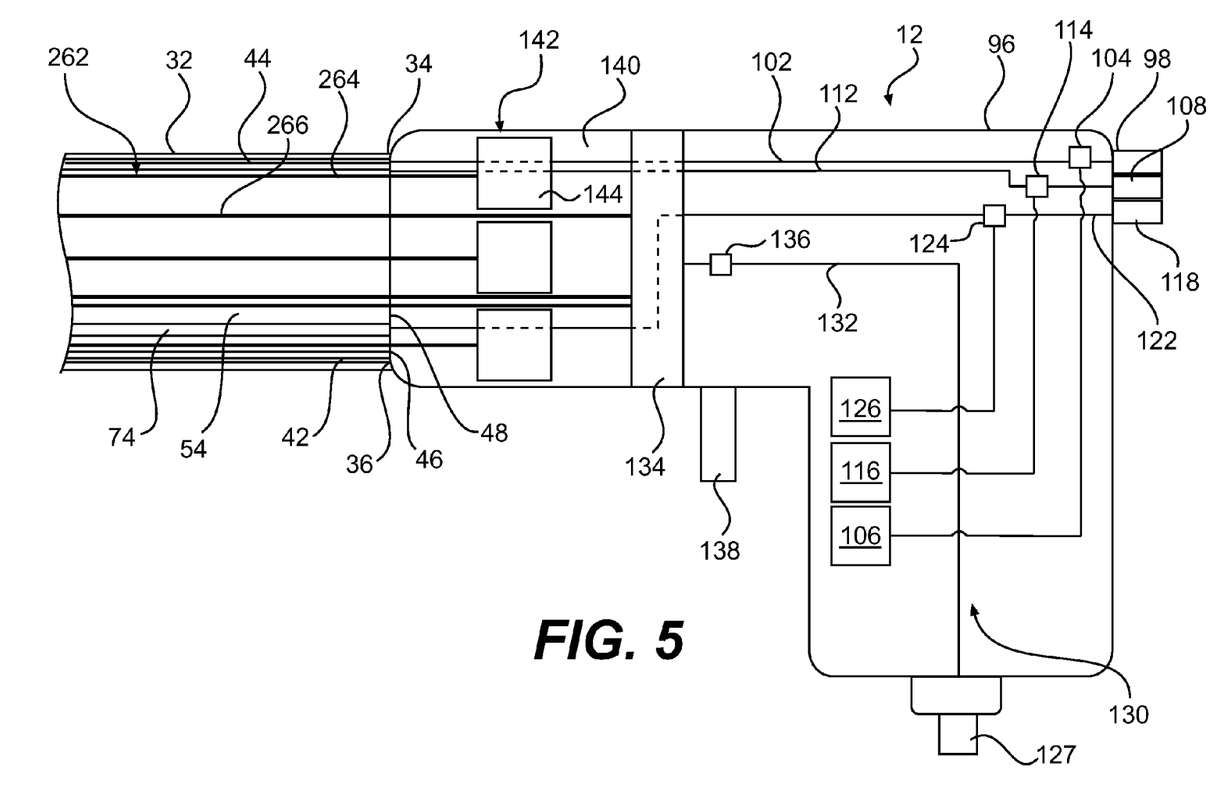
FIG. 5 is a side schematic view of an exemplary handle assembly, according to aspects of the present disclosure.

FIG. 5 is a schematic view of the handle assembly 12. The handle assembly 12 may include an aspiration or vacuum lumen 102 extending from the aspiration port 98 to the proximal opening 36 of the second sheath 32, placing the vacuum source 100 in fluid communication with the lumen 42 of the second sheath 32. An aspiration valve 104 may control fluid flow through the aspiration lumen 102. An irrigation fluid lumen 112 may extend from the irrigation fluid port 108 to the proximal opening 48 of the shaft 44, placing the irrigation fluid source 110 in fluid communication with the lumen 54 of the shaft 44. An irrigation fluid valve 114 may control fluid flow through the irrigation fluid lumen 112. An inflation fluid lumen 122 may extend from the inflation fluid port 118 to an inflation tube 74. The inflation tube 74 may extend distally through the lumen 54 of the shaft 44, to the proximal opening 82 of the balloon 78, placing the inflation fluid source 120 in fluid communication with the interior of the balloon 78. An inflation fluid valve 124 may control fluid flow through the inflation fluid lumen 122.

The valves 104, 114, and 124 may control fluid flow through their respective lumens by moving between open and closed positions, and to positions therebetween. The aspiration actuator 106, irrigation fluid actuator 116, and inflation fluid actuator 126, may be used to control operation of the aspiration valve 104, irrigation fluid valve 114, and inflation fluid valve 124, respectively.

The handle assembly 12 may also include an RF energy conduction assembly 130, including one or more conductors 132 for electrically coupling the RF energy connector and RF 127 and energy source 128, to the proximal sections of the electrodes 58. Energy source 128 may be an RF energy source which may include the ability to turn the RF energy on or off as well as the ability to control the energy when supplied. In FIG. 5, proximal sections are shown as having the features of the proximal sections 262. It should be understood, however, that the proximal sections may include the features of the proximal section 362. A switch 136 may control current flow through the RF energy conduction assembly 130. The RF energy actuator or trigger 138 may be used to control the opening, closing, and/or other adjustment of the switch 136.

The distal portion of the handle housing 96 may include a rotation member 140. The rotation member 140 may be rotatable relative to the rest of the housing 96. The rotation member 140 may be rotated manually by a user, or rotated by a motor or similar powered device (not shown) mounted on or in the handle housing 96. A rotational connector or bearing assembly 134 may rotatably couple the rotation member 140 the rest of the housing 96. The aspiration lumen 102, irrigation fluid lumen 112, inflation fluid lumen 122, and RF energy conductor 132 may extend through the rotational connector 134.

The second sheath 32, shaft 44, and electrodes 58 may be coupled to the rotation member 140. By rotating the rotation member 140, the user may rotate the second sheath 32, shaft 44, and electrodes 58 about the longitudinal axis of the shaft 44. Each of the lumens 102, 112, and 122, and the RF energy conductor 132, may include enough slack to allow the rotation member 140 to rotate through a predetermined extent of rotation.

Alternatively, the rotation member 140 may be fixedly coupled to the housing 96, so that the rotation member 140 may not rotate relative to the housing 96. Rather, the entire housing 96 may be rotated relative to the first sheath 18 to rotate the shaft 44. As another alternative, the second sheath 32 may not rotate relative to the housing 96, and a motor, knob, or other suitable actuator (not shown) may be provided on or in the rotation member 140 for rotating the rotation member 140, and thus the rotatable shaft 44 and the electrodes 58, relative to the second sheath 32 and the housing 96. In embodiments of the medical device 10 including the inner shaft 570 and outer shaft 544, or the inner shaft 670 and outer shaft 644, the inner and outer shafts may be rotated about their longitudinal axes in a manner similar to the way the rotatable shaft 44 is rotated about its longitudinal axis.

At least a portion of the proximal sections (FIGS. 2A and 2B) of the electrodes 58 may be coupled to electrode adjustment actuators 144 of the electrode adjustment mechanism 142. The electrode adjustment actuators 144 may be configured to push or pull the proximal sections to extend or retract the end sections of the electrodes 58, thus controlling the lengths of the end sections. For example, in embodiments including the proximal sections 262, at least one of the legs 264 and 266 may be coupled to the electrode adjustment actuator 144. In embodiments including the proximal section 362, the leg 364 may be coupled to the electrode adjustment actuator 144. In embodiments including the inner shaft 570 and the outer shaft 544, or the inner shaft 670 and the outer shaft 644, the electrode adjustment actuators 144 may be configured to slide the inner shaft relative to the outer shaft, in addition to extend or retract the end sections of the electrodes 58.

Figure 6A:
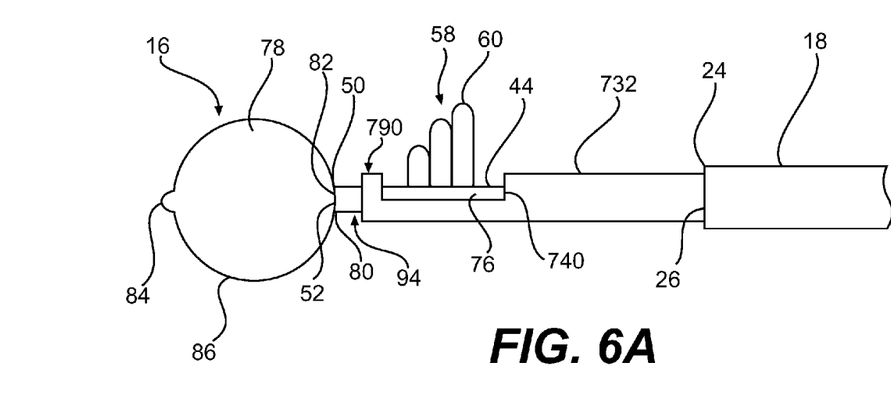
FIG. 6A is a side view of a portion of an exemplary medical device, according to aspects of the present disclosure.

FIG. 6A is a side view of an exemplary alternative embodiment of the medical device 10. The shaft assembly 14 may include a second sheath 732 configured to extend through the first sheath 18. The second sheath 732 may extend distally from the distal opening 26 at the distal end 24 of the first sheath 18. The distal section of the second sheath 732 forms a spacer 790 for positioning the medical device 10 in the subject's body, in a manner similar to the spacer 90 of FIG. 1. The second sheath 732 may include a lumen similar to the lumen 42, and a slot or side opening 740. The shaft 44 may extend through the lumen of the second sheath 732, and the electrodes 58 may extend through the slot 740.

Figure 6B:
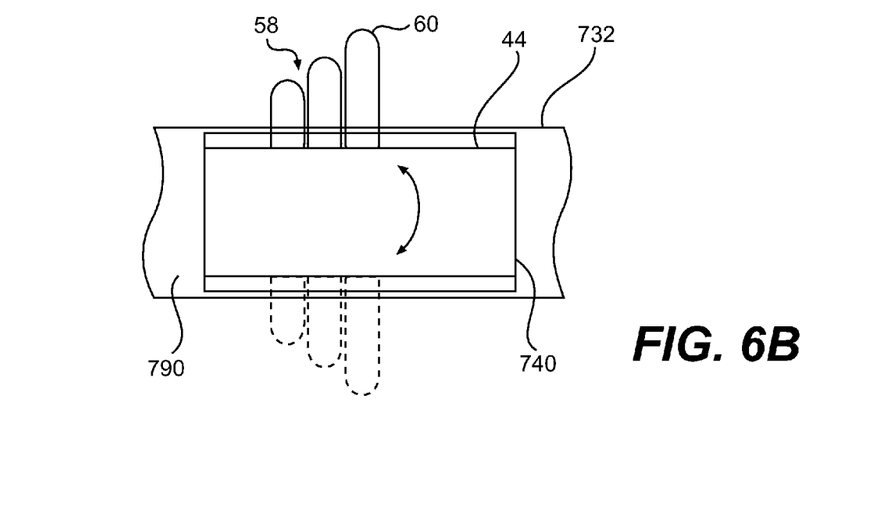
FIG. 6B is a close-up top view of the portion of the medical device from FIG. 6A, according to aspects of the present disclosure.

FIG. 6B is a close-up side view of the slot or side opening 740 in the second sheath 732. The loops 60 extend outwards through the slot 740 of the second sheath 732 from the side openings 740 in the shaft 44. When the shaft 44 is rotated relative to the second sheath 732, the electrodes 58 may travel through an arc corresponding to the rotation of the shaft 44. Edges of the slot 740 may limit over-rotation of the electrodes 58. A 360° removal (e.g., ablation and/or resection) of target tissue surrounding the shaft 44 may be achieved using the electrodes 58 by rotating the second sheath 732 in combination with rotating the shaft 44. It is contemplated that the shaft 44 may be replaced by the inner and outer shafts 570 and 544, or the inner and outer shafts 670 and 644, shown in FIGS. 3A-3D. It is also contemplated that the electrodes 58 may include the features of the wire loops 68 or ribbons 468, shown in FIGS. 2A, 2B, and 3A-3D. It is also contemplated that one or more of the side openings in the shaft 44 and one or more of the electrodes 58 may be aligned along the length of the shaft 44. Alternatively, one or more of the side openings of the shaft 44 and one or more of the electrodes 58 may be circumferentially displaced or offset from one or more of the others.

Figure 7:
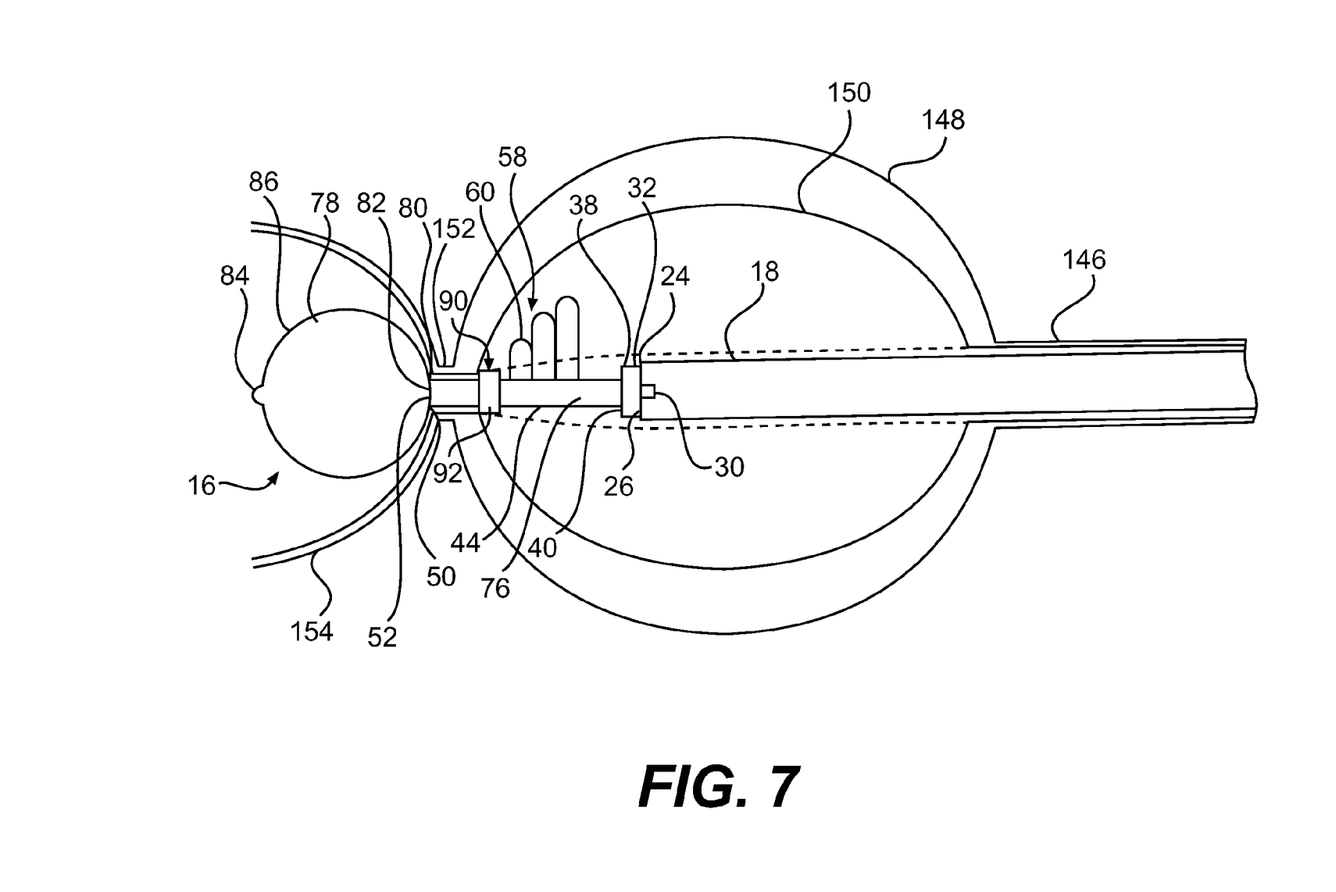
FIG. 7 is a schematic illustration of an exemplary medical device in use, according to aspects of the present disclosure.

FIG. 7 illustrates the medical device 10 of FIG. 1 in use, according to aspects of the present disclosure. During use, the medical device 10 may be inserted through a body lumen, such as a subject's urethra 146. Insertion may include inserting the first sheath 18 through the subject's urethra 146 to a target area. The first sheath 18 may be, for example, a cystoscope. Positioning of the first sheath 18 may be assisted through use of the imaging device 30.

The medical device 10 may be housed in the first sheath 18 during insertion of the first sheath 18, or may be inserted through the first sheath 18 after the first sheath 18 has already been inserted into the subject. During insertion of the medical device 10 through the first sheath 18, the balloon 78 may be uninflated, and/or end sections of the electrodes 58 may be at least partially retracted toward the shaft 44, inner shaft 570, or inner shaft 670. Additionally or alternatively, end sections of the electrodes 58 may be at least partially extended from the shaft 44, inner shaft 570, or inner shaft 670, and may be bent towards the shaft 44 by inner surfaces of the first sheath 18.

The distal section of the medical device 10 may be advanced through the first sheath 18 to the target area. The distal section may be extended out from the distal end 24 of the first sheath 18. The user may maneuver the distal section of the medical device 10 into position at the target area with the help of the imaging device 30. The user may position the medical device 10 such that the balloon 78 is within the subject's bladder 154 on one side of the subject's bladder neck 152, and the spacer 90 or 790 is within the subject's prostate 148 on the opposite side of the bladder neck 152. The shaft 44, inner shaft 570, or inner shaft 670 may be surrounded by unwanted tissue.

The user may actuate the inflation fluid actuator 126 to open the inflation fluid valve 124, and allow inflation fluid to flow from the inflation fluid source 120 to the interior of the balloon 78, through the inflation fluid lumen 122 and the inflation tube 74. Engagement of the inflated balloon 78 and the spacer 90 or 790 with the tissue around the bladder neck 152 may help hold the medical device 10 in a stable position, while also positioning the electrodes 58 in a predetermined location within the prostate 148. The tissue around the bladder neck 152 may occupy the gap 94 between the inflated balloon 78 and the spacer 90 or 790. If desired, the inner shaft 570 may be slid longitudinally relative to the outer shaft 544, or the inner shaft 670 may be slid longitudinally relative to the outer shaft 644, using the electrode adjustment actuator 144, to move the electrodes 58 into a predetermined location in the prostate 148. Proper positioning may also be achieved by rotating the rotation member 140. Proper positioning may be confirmed by the user using the imaging device 30. In addition, an external imaging system such as fluoroscopy or ultrasound may be used to confirm the position of any section or component of the medical device 10.

While the inner shaft 570 and the outer shaft 544 may be coupled to the rotation member 140, so they may rotate as a unit with the rotation member 140, the inner shaft 570 may be longitudinally slidable relative to the outer shaft 544 and the rotation member 140. For example, one of the rotation member 140 and the inner shaft 570 may include a longitudinally-extending groove (not shown), while the other of the rotation member 140 and the inner shaft 570 may include a protrusion (not shown) configured to fit within, and slide longitudinally along, the groove. Side portions of the groove may contact sides of the protrusion, so that relative rotation between the protrusion and the groove is prevented. The inner shaft 670 and the outer shaft 644 may include features similar to the inner shaft 570 and the outer shaft 544, to facilitate longitudinal sliding of the inner shaft 570 and rotation of the inner shaft 570 and the outer shaft 544 as a unit.

Once the medical device 10 is in position, the lengths the electrodes 58 extend from the shaft 44, inner shaft 570, or inner shaft 670, may be independently adjusted by using the electrode adjustment actuators 144 to independently pull or push on proximal sections of the electrodes. Additionally or alternatively, the electrodes 58 may be adjusted together as a unit. By pushing on the proximal section of one of the electrodes 58, the length that electrode 58 extends from the shaft 44, inner shaft 570, or inner shaft 670 may be increased. By pulling on the proximal section of one of the electrodes 58, the length that electrode 58 extends from the shaft 44, inner shaft 570, or inner shaft 670 may be decreased. It is contemplated that the electrodes 58 may each be adjusted so that their end sections are in contact with the undesired tissue in the prostate 148.

The electrodes 58 may be supplied with RF energy from the RF energy source 128 by actuating the RF actuator 138 to adjust the switch 136. When energized, the electrodes 58 may ablate and/or resect the unwanted tissue. Rings or bands of unwanted tissue may be ablated and/or resected by rotating the shaft 44, inner shaft 570, or inner shaft 670, to move the energized electrodes 58. Longitudinal strips of unwanted tissue may be ablated and/or resected by longitudinally moving the shaft 44, inner shaft 570, or inner shaft 670, to move energized the electrodes 58. Helical arcs of unwanted tissue may be ablated and/or resected by rotating and longitudinally moving the shaft 44, inner shaft 570, or inner shaft 670, to move the energized electrodes 58. The exposed lengths of the energized electrodes 58 may also be adjusted to provide the user with additional control during tissue removal. As such, the user may remove unwanted tissue so as to achieve a predetermined profile for the inner surface 150 of the prostate 148, while avoiding damaging healthy tissue. An almond-shaped profile is shown in FIG. 7, with the initial profile of the inner surface 150, prior to ablation and/or resection, being shown with dashed lines. The user may utilize the imaging device 130 to adjust and control the electrodes 58 to achieve predetermined profiles.

Irrigation fluid may be released into the treatment region from the side openings 56 in the shaft 44, the side openings 572 in the inner shaft 570, or the side openings 672 in the inner shaft 670, to cool the treatment region, wash off ablated and/or resected tissue or other debris, and/or to rinse off the imaging device 130. The user may control the release of the irrigation fluid by selectively actuating the irrigation fluid actuator 116. The user may remove the irrigation fluid, tissue, or other debris from the treatment region by selectively actuating the aspiration actuator 106. When the aspiration valve 104 is open, the irrigation fluid, tissue, or other debris may be drawn into the opening 40 of the second sheath 32 or the opening 740 of the second sheath 732, through the lumens 42 and 102, and out the aspiration port 98. When the treatment is completed, the insertion steps may be reversed to remove the medical device 10 from the subject's body.

Although the embodiments described above are disclosed in the context of cystoscope, those skilled in the art will understand that the principles disclosed above can be applied to other types of devices and can be implemented in different ways without departing from the scope of the invention as defined by the claims. In particular, constructional details, including manufacturing techniques and materials, are well within the understanding of those of ordinary skill in the art and have not been disclosed in detail herein. These and other modifications and variations are well within the scope of the present disclosure and can be envisioned and implemented by those of ordinary skill in the art.

Moreover, while specific embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of the various embodiments. Combinations of the above embodiments, and other embodiments not specifically described herein, will be apparent to those of ordinary skill in the art upon reviewing the present disclosure. Further, one or more features described in one of the above-described embodiments, may be used with one or more features described in any of the other above-described embodiments.

Other embodiments of the present disclosure will be apparent to those skilled in the art from consideration of the specification and practice of the embodiments disclosed herein. It is intended that the specification and examples be considered as exemplary only, and departure in form and detail may be made without departing from the scope and spirit of the present disclosure as defined by the following claims.

The medical device may include a lumen or lumens to allow additional devices to be delivered through the medical device. For example, a central lumen in the medical device may be used to deliver a laser fiber or a morcellator to assist in the destruction and/or removal of tissue from the ablation and/or resection site or from a location distal of the electrodes. In some embodiments, once tissue is ablated and/or resected it may be pushed distally with a sheath or with irrigation fluid, for example into the bladder of a patient, and then reduced further in size by use of a morcellator or laser delivered through the medical device. The resulting smaller tissue pieces may be aspiratable though the medical device.

Use of the medical device is not limited to the removal of prostatic tissue. It may be useful in other locations within a patients' body, for example, but not limited to, in a vagina, cervix, uterus, esophagus or rectum.

What is claimed is:
1. A medical device, comprising:
a shaft assembly, including:
 a sheath having a first lumen, and a distal section having a distal opening and a side opening;
 a rotatable shaft extending through the first lumen, the rotatable shaft being rotatable relative to the sheath and having a second lumen, a side opening, and a distal section extendable distally from the distal opening of the sheath; and an electrode extending through the second lumen of the rotatable shaft, the side opening of the rotatable shaft, and radially outwardly from the rotatable shaft, the electrode being movable relative to the rotatable shaft.

2. The medical device of claim 1, wherein the electrode includes a first section extending through the second lumen and the side opening of the rotatable shaft, and a second section extending radially outwardly from the rotatable shaft.

3. The medical device of claim 2, wherein the first section is slidable in the second lumen and the side opening of the rotatable shaft.

4. The medical device of claim 3, wherein proximal sliding of the first section decreases a length of the second section.

5. The medical device of claim 3, wherein distal sliding of the first section increases a length of the second section.

6. The medical device of claim 1, wherein at least a portion of the electrode extends through the side opening of the distal section of the sheath.

7. The medical device of claim 1, wherein the shaft assembly includes an inner sheath extending through the second lumen.

8. The medical device of claim 7, wherein the inner sheath has a third lumen and a side opening, the electrode extends through the third lumen and the side opening of the inner sheath, and the side opening of the rotatable shaft overlaps with the side opening of the inner sheath.

9. The medical device of claim 8, wherein at least one of the inner sheath and the rotatable shaft is longitudinally slidable relative to the other of the inner sheath and the rotatable shaft.

10. A medical device, comprising:
a shaft assembly, including:
  a sheath having a first lumen, and a distal section having a distal opening and a side opening;
  a rotatable shaft extending through the first lumen, the rotatable shaft being rotatable relative to the sheath and having a second lumen, side openings, and a distal section extendable distally from the distal opening of the sheath; and
  a plurality of electrodes including proximal sections extending through the second lumen and the side openings of the rotatable shaft, and distal sections extending radially outwardly from the rotatable shaft, each of the plurality of electrodes being independently movable relative to the rotatable shaft.

11. The medical device of claim 10, wherein the proximal sections are slidable in the second lumen and the side openings, of the rotatable shaft to move the distal sections.

12. The medical device of claim 11, wherein sliding the proximal sections proximally reduces lengths of the distal sections, and sliding the proximal sections distally increases the lengths of the distal sections.

13. The medical device of claim 10, wherein the shaft assembly further includes an inner sheath extending through the second lumen.

14. The medical device of claim 13, wherein the inner sheath has a third lumen and a side opening, the electrodes extend through the third lumen and exit from the third lumen through the side opening of the inner sheath, and the side openings of the rotatable shaft overlap with the side opening of the inner sheath.

15. The medical device of claim 14, wherein each of the electrodes forms a loop.

* * * * *